United States Patent [19]  [11] Patent Number: 4,855,486
Kalbag  [45] Date of Patent: Aug. 8, 1989

[54] BLOCKED, MARKED AMINO ACIDS

[76] Inventor: Suresh M. Kalbag, 922 Blazingwood Ave., Cupertino, Calif. 95104

[21] Appl. No.: 157,659

[22] Filed: Feb. 19, 1988

Related U.S. Application Data

[62] Division of Ser. No. 869,098, May 30, 1986, Pat. No. 4,755,558.

[51] Int. Cl.$^4$ ............... C07D 209/52; C07C 103/84; A61K 31/40; A61K 31/195
[52] U.S. Cl. .................. 560/158; 560/160; 560/169; 560/171; 546/184; 546/290
[58] Field of Search ............ 560/169, 171, 158, 160; 546/184, 290

[56] References Cited

U.S. PATENT DOCUMENTS

| | | | |
|---|---|---|---|
| 3,334,969 | 8/1967 | Catravas | 436/89 |
| 3,346,486 | 10/1967 | Winter et al. | 436/89 |
| 3,518,240 | 6/1970 | Tilak et al. | 530/334 |
| 3,578,164 | 5/1971 | Johnson | 530/337 |
| 3,717,436 | 2/1973 | Penabsi et al. | 436/89 |
| 3,814,732 | 6/1974 | Wang | 530/334 |
| 3,925,267 | 12/1978 | Coupek et al. | 525/54.11 |
| 4,076,913 | 2/1978 | Walker et al. | 525/54.11 |
| 4,105,789 | 8/1978 | Ondetti et al. | 560/171 |
| 4,283,504 | 8/1981 | Campbell et al. | 525/54.11 |
| 4,515,920 | 5/1985 | Erickson | 530/334 |
| 4,582,875 | 4/1986 | Ngo | 525/54.1 |
| 4,623,484 | 11/1986 | Carpino et al. | 530/334 |
| 4,624,962 | 11/1986 | Henning et al. | 560/169 |

OTHER PUBLICATIONS

Tam et al., Synthesis, 12: 955–957 (1979).
Merrifield, J. American Chem. Soc., 85: 2149–2154.
Meienhofer, "Large Scale Peptide Synthesis: A Review", 18th European Symposium, Stockholm, Sweden.
Esko et al., Acta Chem. Scand., 22: 3342–3344 (1986).
Brunfeldt et al., Acta Chem. Scand., 23: 2906–2907 (1969).
Dorman, Tetrahedron Letters, 2519–2521 (1969).
Kaiser et al., Anal. Biochem., 34: 595–598 (1970).
Felix, Anal. Bio. Chem., 52: 377–381 (1973).
Gisin, Helv. Chim. Acta, 56: 1476–1482 (1973).
Frankhauser et al., Helv. Chim. Acta, 57: 271–277 (1974).
Christensen, Acta Chemica Scandinavia B, 33: 763–766 (1979).
Kaiser et al., Anal. Chim. Acta, 118: 149–151 (1980).
Sarin et al., Anal. Biochem., 117: 147–157 (1981).
March, Advanced Organic Chemistry: Reactions Mechanisms, and Structure, pp. 746–780, McGraw-Hill, N.Y., N.Y. (1968).
DePuy et al., Chem. Rev., 60: 431–457 (1960).
Mitchell et al., J. Amer. Chem. Soc., 98: 7357–7362 (1976).
Kalbag et al., Peptides: Structure and Function, Proceedings of the 9th American Peptide Symposium, 269–272 (1985).
Kalbag et al., Abstract, Ninth American Peptide Symposium.

Primary Examiner—John Kight
Assistant Examiner—Nathan M. Nutter
Attorney, Agent, or Firm—Sheldon & Mak

[57] ABSTRACT

A method is provided for quantitatively monitoring the deprotection and coupling reactions employed in the solid phase synthesis of peptides. The method entails synthesizing a peptide on a support matrix that has a first marker associated therewith. The amino acids employed in the peptide synthesis procedure have a second marker attached thereto, which can be the blocking group used for the amino acid. After the coupling of deprotection step a portion of the support matrix is processed to release first and second identifers from the first and second markers, respectively. The completeness of the coupling or deprotection step can be determined by comparing the relative amounts of the detected first and second identifiers. Novel compositions of matter are used in or produced during this method, including support matrixes having pyrolyzable markers attached thereto.

11 Claims, No Drawings

BLOCKED, MARKED AMINO ACIDS

This is a division of application Ser. No. 869,098, filed May 30, 1986, now U.S. Pat. No. 4,755,558.

BACKGROUND

The present invention relates to methods for forming a peptide on a support matrix.

The Merrifield method of solid phase peptide synthesis is an extremely useful synthetic tool. In the Merrifield method, a peptide attached to a support matrix is lengthened by coupling with an amino acid. The N-terminus of the amino acid is protected by a blocking group such as a BOC group (t-butoxycarbonyl). The lengthened peptide is then decoupled by removing the blocking group, and then the coupling reaction is repeated. A problem with solid phase peptide synthesis is the determination of when the coupling and deprotection reactions are complete. The completeness of these reactions is essential to peptide synthesis, since an incomplete coupling or deprotection reaction can lead to deletion of an amino acid in the desired sequence. These deletions can vary from trace to significant amounts.

Numerous methods for monitoring the completeness of the deprotection and coupling reactions have been reported. For example, the Kaiser (ninhydrin) test is convenient, rapid (requires about 5 minutes to run) and well documented. For these reasons, the Kaiser test is the most widely used of the qualitative monitoring methods. In the Kaiser test, a reagent is reacted with the unblocked supported peptide to produce a purple product, the intensity of the purple color qualitatively indicating the amount of decoupling The Kaiser test has disadvantages. For example, it has been shown to give false positive results for complete coupling. In addition, the Kaiser test lacks sensitivity with respect to the degree of deprotection of BOC-amino acids because the intensity of Ruhemann's purple is noted from about 50 to about 100 percent free amino groups. Another drawback to the Kaiser test is its lack of good color resolution for the deprotection of secondary amino acids. More particularly, the deprotection of proline, hydroxyproline, and sarcosine gives a brown color instead of purple.

Another monitoring method uses chloromil. The chloromil method, like the Kaiser method, is inherently inaccurate since it relies on color differentiation. The reason for this is that in dilute solutions, faint amounts of color are difficult to detect with the naked eye.

Two common quantitative tests, the picric acid titration and the quantitative ninhydrin test, have advantages over the qualitative Kaiser and chloromil tests in that they give quantitative information about the degree of deprotection or coupling during peptide synthesis. However, both of these quantitative methods suffer as synthetic monitoring tools due to (1) the length of time (about 2 hours) required to complete the test because of the need to dry and accurately weigh the resin peptide samples; (2) the need for a highly skilled technician to obtain reproducible results; and (3) the lack of sensitivity in determining the completeness of the deprotection and coupling reactions. Since peptide chains can have 30 or more amino acids, a monitoring test that requires in excess of 2 hours per amino acid added to the support is not commercially feasible on a routine basis.

Accordingly, it would be very desirable to have a quantitative method for monitoring the completeness of the coupling and deprotection reactions employed in solid phase peptide synthesis where the method (1) requires a relatively short period of time to perform; (2) does not require the use of a highly skilled technician to obtain reproducible results; and (3) is sensitive to the completeness of both the deprotection and coupling reactions.

SUMMARY

The present invention provides a system that satisfies these needs. More particularly, a method according to the present invention for monitoring the completion of coupling and deprotection reactions employed in solid phase peptide synthesis is advantageous in that (1) the length of time required for monitoring is short because there is no need to dry or accurately weigh samples; (2) the method does not require a highly skilled technician in order to obtain reproducible results; and (3) the method is sensitive to the degree of completeness of both the deprotection and coupling reactions.

A method embodying features of the present invention comprises the following steps:

A. Selection

A support matrix is selected, the support matrix having a marker associated therewith, and having a group capable of bonding to an amino acid. The support matrix can be processed to release a first detectable identifier from the marker. The marker is generally attached to the support matrix, although it can be attached to a second matrix where a blend of the support matrix and the second matrix is used.

B. Coupling

A supported blocked amino acid is formed by reacting a plurality of the selected support matrix with a blocked amino acid to attach the blocked amino acid to the support matrix. The supported amino acid can be processed to release a second detectable identifier different from the first identifier. The blocked amino acid has an N-terminus blocking group attached thereto.

The supported blocked amino acid can be treated to release the N-terminus blocking group and unblock the amino acid thereby forming a supported unblocked amino acid for reaction with another blocked amino acid. This treatment step can be performed without deleteriously affecting the marker, i.e., the marker can still be processed to release the first detectable marker. The unblocked amino acid is available to react with another N-terminus protected amino acid to form a peptide.

C. Processing

At least a portion, and usually only a small portion, of the coupling step reaction product is processed to release the first and second identifiers. Preferably the marker is chosen so that processing is effected by pyrolyzing the coupling step reaction product. Processing is effected without deleteriously affecting the peptide forming on the support.

D. Detection and Comparison

The first and second identifiers are detected. The respective amounts of the detected identifiers are compared to determine whether the coupling step is complete, i.e., whether the support matrix has any group which is capable of and available to react with an N-terminus blocked amino acid. If coupling is not complete, steps B through D are repeated until substantially complete coupling is achieved.

E. Deprotection

The remainder of the supported blocked amino acid, i.e., the portion not processed in step (C), is treated to remove the N-terminus blocking group from the amino acid to form a supported unblocked amino acid.

F. Processing

At least a portion, and generally only a small portion, of the supported, unblocked amino acid is processed to release the first and second identifiers. Processing is effected without deleteriously affecting the peptide forming on the support.

G. Detection and Comparison

The first and second identifiers are detected and a comparison is made of the respective amounts of the detected identifiers. The purpose of this comparison is to determine whether the deprotection step is complete, i.e., whether any support matrix has any N-terminus protected amino acids attached thereto.

Steps E–G can be repeated until deprotection is compete. In general, steps B–G are repeated until the desired peptide is formed on the support matrix.

There are several compositions that can be employed in and can be produced by this method. A first composition of matter comprises a support matrix having a peptide and a marker attached thereto. The peptide has a terminal amino acid with an N-terminus blocking group attached thereto. This composition of matter can be treated, without deleteriously affecting the marker, to release the N-terminus blocking groups and to thereby make the terminal amino acid available to react with another N-terminus blocked amino acid to lengthen the peptide. In addition, the composition can be processed to release a first detectable identifier from the marker and a second detectable identifier from the blocking group. The first and second identifiers are different.

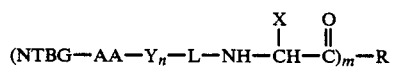

where:
R is the support matrix;
m and n are positive integers;
X is a side chain comprising the marker;
L is a linking group;
Y is an amino acid;
AA is the terminal amino acid of the peptide; and
NTBG is the N-terminus blocking group.
X can be:

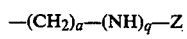

where
a is 0 or a positive integer;
q=0 or 1; and
Z is the marker.
Z can be:

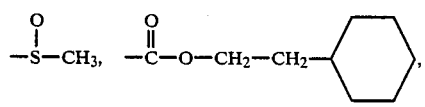

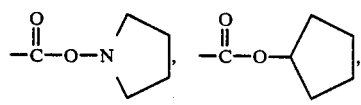

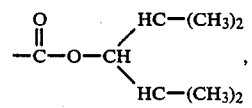

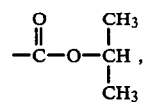

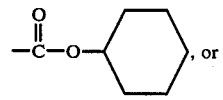

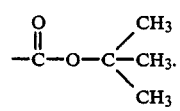

Preferred markers where the processing is by pyrolysis have the formula

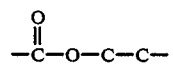

where a beta carbon has at least one hydrogen attached thereto. There can be more than one beta carbon. The more hydrogen attached to a beta carbon, the more readily does the marker release an identifier by pyrolysis. Pyrolysis generally breaks the bond between the oxygen and the alpha carbon releasing as the identifier a composition including the alpha carbon, the beta carbon(s), and substituents attached thereto.

A second composition of matter comprises the first composition where the terminal amino acid is devoid of an N-terminus blocking group, i.e. the first composition after the blocking group is removed. Accordingly, the terminal amino acid of this second composition of matter is available to react with another N-terminus blocked amino acid.

A third composition of matter is the support by itself with the markers attached. This composition has the formula:

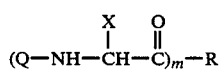

where R, m, and X are defined above and Q is H or a linking group. X can be selected from the group consisting of:

a is 0 or a positive integer; and Z, the marker is selected from the group consisting of

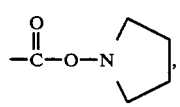

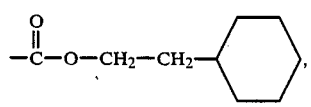

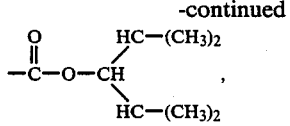

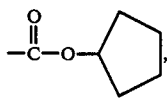

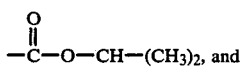

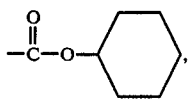

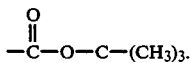

Alternatively, X can be selected from the group consisting of:
—(CH$_2$)$_a$—Z, —(CH$_2$)$_a$—NH—Z,
—(CH$_2$)$_a$—CHZ—(CH$_2$)$_a$—CH$_3$,
and

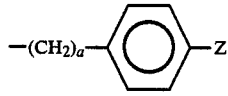

wherein a is as defined above and Z is selected from the group consisting of —O—trityl, —S—trityl, —O—pixyl, —S—pixyl, and homologs and analogs thereof.

A further composition of matter is a marked amino acid having the formula:

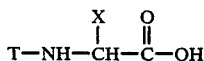

wherein T is H or an N-terminus blocking group and X is as defined above.

These and other features, aspects, and advantages of the present invention will become better understood with reference to the following description and appended claims.

DESCRIPTION

In accordance with the present invention, an internal standard or first marker is associated with a support matrix. This support matrix is present in a reaction medium where a solid phase peptide synthesis is conducted.

In addition, a second marker is associated with the amino acids employed to synthesize the desired peptide. The first and second markers, upon processing, release a first and second identifier, respectively. These identifiers are different.

By comparing the relative amounts of the first and second identifiers, a determination can be made as to the completion of the coupling and/or deprotection steps employed in solid phase peptide synthesis. The ability to perform this comparison obviates the need to either dry or weigh the resin peptide sample. The result is that the quantitative monitoring procedure of the present invention for monitoring the completion of coupling and deprotection reactions is expeditious, does not require a highly skilled technician, and is sensitive to the completeness of both the deprotection and coupling reactions.

As noted above, a support matrix having a first marker or internal standard associated therewith is employed in the present invention. The first marker must be capable of being attached to a matrix and must be stable to peptide synthesis conditions. This matrix can be either the support matrix or a separate matrix used in association with the support matrix.

The first and second markers must also be capable of being directly or indirectly detected. For example, the markers can be groups which, upon pyrolysis, produce detectable product or identifiers. Similarly, the markers can be groups which, upon treatment, produces identifiers which are chromophoric products. As used herein, chromophoric products include substances that can be detected in the visible and non-visible ranges.

Accordingly, as used herein, the term pyrolytic marker indicates a group which upon thermal decomposition, of at least a portion thereof, releases a composition or identifier capable of being detected such as by gas chromatography.

In addition, as used herein, the term chromographic marker indicates a group, wherein at least a portion thereof upon processing (e.g. by treatment with a chemical substance) releases a composition or identifier capable of being detected by spectroscopy.

As also indicated in the above definitions the identifier consists of at least a portion of the marker.

Support matrixes having a first marker attached thereto can have the formula I

wherein R is a support matrix; m is a positive integer; Q is H or a linking group; and X is selected from the first group consisting of —(CH$_2$)$_a$—NH—Z, —(CH$_2$)$_a$—Z, and

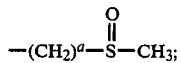

a is 0 or a positive interger; and Z is selected from the group consisting of

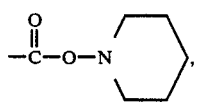

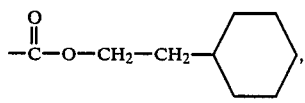

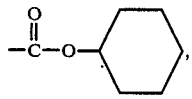

-continued

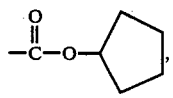

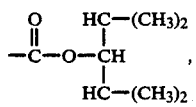

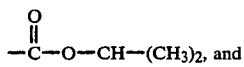

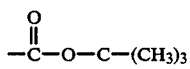

Exemplary support matrixes include, but are not limited to styrene and divinylbenzene copolymers, polyamides, polyacrylate, polymethylmethacrylate, polysaccharides, phenoliic resins, silica, porous glass, and polyacrylamides. A preferred support matrix is copoly(styrene-1%-divinylbenzene) resin.

Various linking groups, designated as L, can be used in the support matrix of formula I. These linking groups include, but are not limited to,

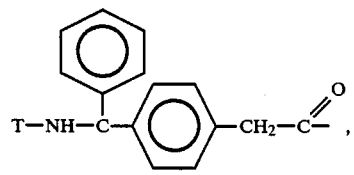

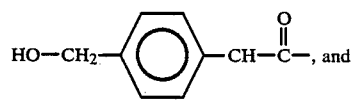

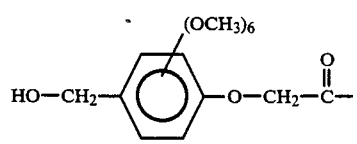

wherein T is H or an amino blocking group and b is 0 or 1. Because the extent of its coupling can be determined, it is preferred that the linking group present in the support matrix of formula I have the formula.

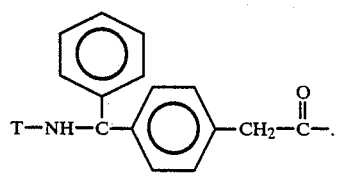

In order to react with an N-terminus blocked amino acid, T must be H.

In the support matrix of formula I, X can also be selected from a second group consisting of —(CH$_2$)$_a$—Z, —(CH$_2$)$_a$—Z, —(CH$_2$)$_a$—CHZ—(CH$_2$)$_a$—CH$_3$, and

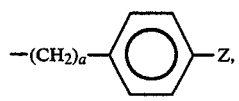

wherein a is as defined above and Z is selected from the group consisting of —O—trityl, —S—trityl, —O—pixyl, —S—pixyl, and homologs and analogs thereof.

Homologs and analogs of trityl include, but are not limited to, tris(4-hydroxyphenyl)methyl, tris(4-aminophenyl)methyl and dimethoxytrityl.

Exemplary amino blocking groups include, but are not limited to, t-butyloxycarbonyl (BOC), 2-(4-biphenylyl)-2-propyloxy carbonyl, alpha-2,4,5-tetramethylbenzyloxy carbonyl, 2-phenyl-2-propyloxycarbonyl, 2-(3,5-dimethoxyphenyl)-2-propyloxy carbonyl, fluorenyl methyloxy carbonyl, 3-nitro-2-pyridine sulfenyl, and homologs and analogs thereof.

When X is selected from the first group consisting of —(CH$_2$)$_a$—NH—Z, —(CH$_2$)$_a$—Z, and

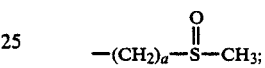

the side chain can have a pyrolytic group attached thereto. When the side chain has a pyrolytic group attached thereto, it is preferred that the amino blocking group be capable of yielding a distinguishable detectable product upon pyrolysis. Such amino blocking groups include but are not limited to t-butyloxycarbonyl, 2-(4-biphenylyl)-2-propyloxycarbonyl, alpha-2,4,5-tetramethylbenzyloxy carbonyl, 2-phenyl-2-propyloxycarbonyl, 2-(3,5-dimethoxyphenyl)-2-propyloxycarbonyl groups.

When X is selected from the second group consisting of —(CH$_2$)$_a$—NH—Z, —(CH$_2$)$_a$—Z, —(CH$_2$)—CHZ—(CH$_2$)$_a$—CH$_3$, and

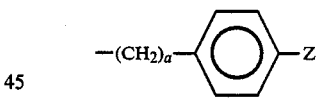

the side chain can have a chromophoric group attached thereto. When the side chain has a chromophoric group attached thereto, it is preferred that the amino blocking group be capable of yielding a distinguishable product upon treatment. Such amino blocking groups include, but are not limited to, flourenyl methoxy carbonyl and 3-nitro-2-pyridine sulfenyl groups.

When a pyrolytic method embodying features of the present invention is used, a preferred marked support matrix of formula I is selected from the group consisting of

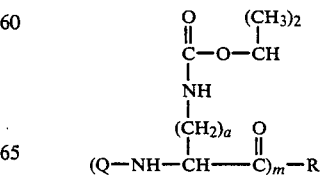

and

-continued

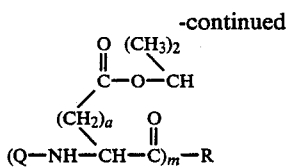

wherein Q, a, and R are as defined above. These marked support matrixes are preferred because the —CH—(CH₃)₂ group readily yields a detectable identifier upon pyrolysis.

Because of their commercial availability, it is also preferred that a be 1 to about 6. For the same reason, a is more preferably 1 to about 4.

The marked support matrix of formula I can be prepared by several techniques. In one technique, a blocked, marked amino acid is reacted with a support matrix. The blocked marked amino acid can have the formula II $$\underset{\underset{T-NH-CH-C-OH}{}}{\overset{X\quad O}{|\quad\|}} \tag{II}$$

wherein X is as defined above and T, which in general can be H or an N-terminus blocking group, is an N-terminus blocking group.

N-terminus blocking groups include, but are not limited to, the same groups set forth above with respect to amino blocking groups.

Preferred blocked, marked amino acids having a pyrolytic group attached thereto have the formula

These blocked marked amino acids are preferred because of the relative ease with which the N-terminus blocking group and the marker pyrolyze to yield distinguishable identifiers.

The blocked, marked amino acid can be prepared by various methods. For example, a blocked amino acid having a pyrolytic marker attached thereto can be obtained by suitable treatment of a N- and C-terminus protected amino acid having a carboxyl group in its side chain. Typical amino acids of this type are aspartic acid and glutamic acid. The following preparation of BOC-beta-isopropyl asparate exemplifies this procedure:

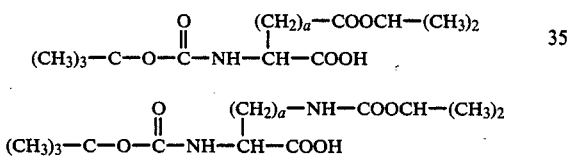

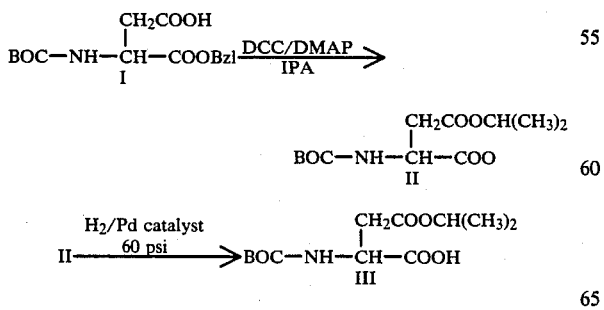

In the above procedure, BOC-alpha-benzyl asparate (BOC is alpha-t-butoxycarbonyl) is esterified with iso-propyl alcohol (IPA) using dicyclohexylcarbodiimide (DCC) and 4-dimethylaminopyridine (DMAP). The resulting diester II is subjected to hydrogensis to produce the desired beta-isopropyl ester III.

Another procedure for preparing BOC-beta-isopropyl asparate can be schematically depicted as follows:

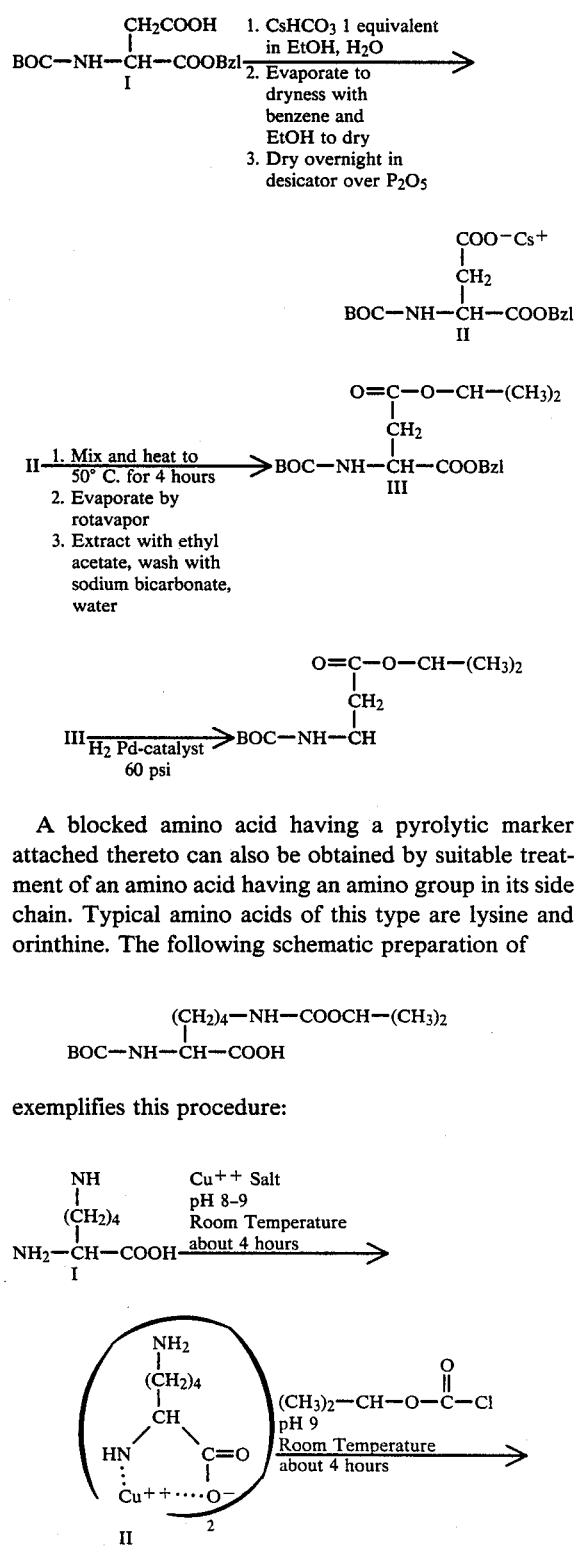

A blocked amino acid having a pyrolytic marker attached thereto can also be obtained by suitable treatment of an amino acid having an amino group in its side chain. Typical amino acids of this type are lysine and orinthine. The following schematic preparation of $$\underset{\underset{BOC-NH-CH-COOH}{|}}{\overset{(CH_2)_4-NH-COOCH-(CH_3)_2}{|}}$$

exemplifies this procedure:

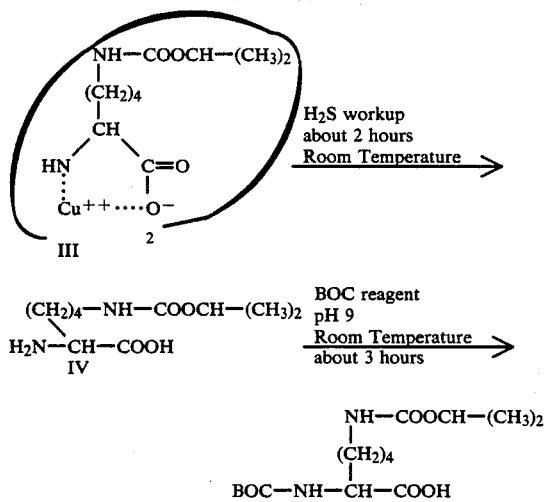

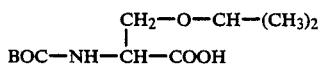

A blocked amino acid having a pyrolytic marker attached thereto can also be obtained by suitable treatment of an amino acid having a hydroxyl group in its side chain. Typical amino acids of this type are serine, threonine and tyrosine. The following schematic preparation of $$\underset{\text{BOC—NH—CH—COOH}}{\overset{\text{CH}_2\text{—O—CH—(CH}_3)_2}{|}}$$

exemplifies this procedure:

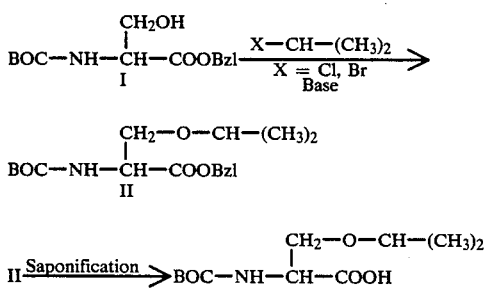

A blocked amino acid having a chromophoric marker attached thereto can be obtained by suitable treatment of an amino acid having a (a) hydroxyl group, (b) amino group, or (c) thiol group in its side chain. Typical amino acids of this type are (a) serine, threonine, tyrosine, (b) ornithine, lysine, and (c) cysteine, respectively. The following discription exemplifies this procedure.

Trityl chloride can be treated in a polar, aprotic solvent (e.g., dioxane, tetrahydrofuran) with an N-terminus and C-terminus protected amino acid. The N-terminus protecting group can be, for example, fluorenyl methoxy carbonyl (FMOC) and 3-nitro-2-pyridine sulfenyl (NPYS). The C-terminus protecting group can be, for example, benzyl ester, methyl ester, ethyl ester, and phenacyl ester. Phenacyl ester is preferred because it can be relatively easily removed from the amino acid. This treatment procedure is conducted in a mild base (e.g., pyridine, leutidine) at a temperature of about 50° to about 60° C. for a minimum of four hours. Thin layer chromotography (TLC) can be used to monitor the reaction.

The above reaction medium is evaporated to dryness and the resulting residue is extracted with ethyl acetate (EtOAc) or methylene chloride (CH$_2$Cl$_2$). The extract is washed with a dilute acid, (e.g., about 0.1 to about 1N HCl). This is followed by a wash with water. The organic layer is first dried with anhydrous sodium sulfate and then evaporated to dryness. The dried product has the trityl group attached to the side chain of the N- and C- terminus blocked amino acid. The free acid can be obtained by saponifying the dried product with a mild base (e.g., about 1N NaOH). However, when phenacyl ester is used, the free acid is obtained by treating the dried product with thiophenol.

Procedures analogous to those set forth above for producing blocked, marked amino acids can be employed to produce other amino acids having different markers and/or diferent side chain groups and/or different N-terminus blocking groups attached thereto.

The support matrix, with which the blocked amino acid of formula II is reacted, has a functional group attached thereto which is capable of reacting with the C-terminus of the blocked amino acid. For example, in the case of support matrixes having a hydroxyl functionality (e.g., phenolic resins, polysaccharides, hydroxymethyl polystyrene), the blocked amino acid is activated by DCC in the presence of an activator (e.g., DMAP) and the support matrix.

This yields a blocked marked amino acid attached to the support matrix. The number of such attachments will depend, in part, upon the number of available hydroxyl groups.

The reagents and by-products are then drained from the support matrix. The support is washed with a solution (e.g., CH$_2$Cl$_2$, dimethyl formamide (DMF), dioxane).

Unreacted hydroxyl groups on the support matrix are now blocked with a 5% solution of phenylisocyanate in CH$_2$Cl$_2$. This blocking step is conducted for about 30 minutes at about room temperature. The reacting mixture is then drained and the support matrix is washed 3 times with CH$_2$Cl$_2$. The N-terminus protecting group is removed from the blocked, marked amino acid that is attached to the support matrix.

In the case of support matrices having an amino functionality (e.g., amino functionalized polystyrene divinylbenzene copolymer, and amino functionalized polyamide), the attachment procedure is the same as that set forth above with the exception that the blocked, marked amino acid does not require an activator to be present in order to react with amino functionalized support matrixes.

The linking group can be attached to N-terminus of the unblocked, marked amino acid, via conventional procedures.

When Q of the support matrix of formula I is H, the initial amino acid of the desired peptide (i.e., the C-terminus amino acid of the peptide to be synthesized) is first attached to the linking group. In such instance, the resulting compound has the formula III

wherein L is a linking group, X$_{sc}$ is an amino acid side chain, and NTBG is the N-terminus blocking group.

In the above formula III, L can be, for example,

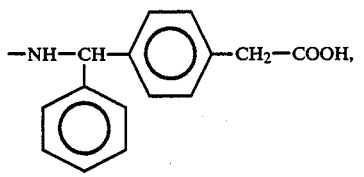

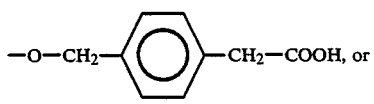

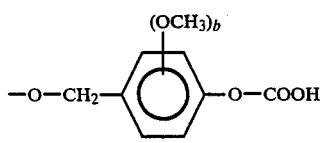

wherein b is 0 or 1. For the reasons set forth above, the first of the above linkers is preferably attached to the support matrix without the initial amino acid being attached thereto. Accordingly, in formula III, L is preferably selected from the group consisting of

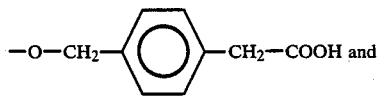

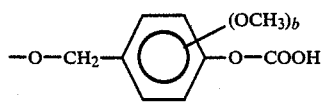

wherein b is as defined above.

NTBG can be any N-terminus protecting group. Exemplary N-terminus protecting groups include, but are not limited to, t-butyloxycarbonyl, 2-(4-biphenylyl)-2-propyloxy carbonyl alpha-2,4,5-tetramethylbenzyloxy carbonyl, 2-phenyl-2-propyloxycarbonyl, 2-(3,5-dimethoxyphenyl)-2-propyloxy carbonyl, fluorenyl methyloxy carbonyl, 3-nitro-2-pyridine sulfenyl, and homologs and analogs thereof. Because ether linking groups, such as:

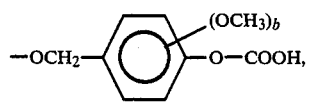

are acid labile, these linkers can only be employed in solid phase peptide synthesis employing neutral or basic conditions. Since some N-terminus blocking groups are removed from N-terminus blocked amino acids under acidic conditions, the N-terminus blocking group employed when an ether linkage is used preferably is capable of being removed under basic or neutral conditions. Exemplary linkers that can be removed under basic or neutral conditions include, but are not limited to, fluorenyl methoxy carbonyl, 3-nitro-2-pyridine sulfenyl, and homologs and analogs thereof.

$X_{sc}$ can be any natural or unnatural amino acid side chain. In addition, $X_{sc}$ can have the second marker attached thereto. Amino acids having the second marker attached to $X_{sc}$ can be prepared by methods analogous to those employed to prepare the amino acids of formula II. In general, the first and second markers are preferably chosen from the same class of markers (i.e. pyrolytic, chromophoric, etc.). The reason for this is that the same type of detection procedure can be employed to determine the first or second markers, respectively. However, the markers are chosen so that the first and second identifiers are different.

Pyrolytic and chromophoric markers attached to $X_{sc}$ can be removed from the synthesized peptide with the same procedure employed to cleave the peptide from the solid support.

Compounds of formula III can be prepared by reacting an N-terminus blocked amino acid with a linking group via conventional procedures. Exemplary linking groups have the formulas

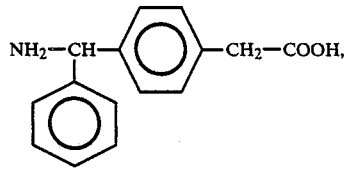

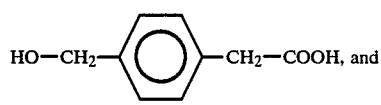

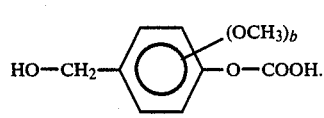

Similarly, when the linking group is attached to the support matrix, as shown in formula I wherein Q is the linking group, an N-terminus blocked amino acid can be reacted with the linking group via conventional procedures employed to couple an amino acid to a solid support.

The thus formed support matrix having the initial amino acid attached thereto has the formula IV

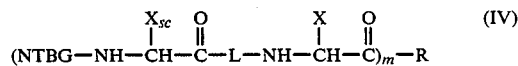

wherein NTBG, $X_{sc}$, L, X, R and m are defined above. In the case of the linking group, L can be more precisely represented by the modified formulas

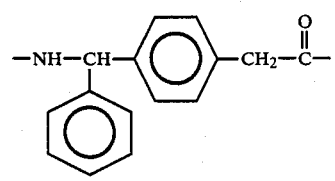

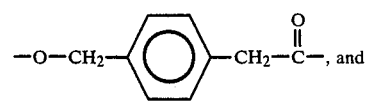

-continued

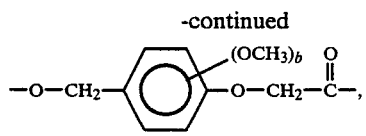

wherein b is as defined previously.

A portion or sample of the support matrixes present after the coupling reaction is then processed to release the first and second identifiers from the first and second markers, respectively. The particular procedure employed depends on the type of first and second markers present.

When both markers are pyrolytic markers, the process employed entails heating the sample to a temperature sufficient to release the first and second identifiers without deleteriously affecting the remainder of the composition. In general any temperature can be employed to release these identifiers provided that the sample does not decompose to release any substance which can interfere with the detection of the first and second identifiers. To prevent such decomposition, the temperature employed is preferably below about 750° C.

Generally, a temperature of about 450° to about 600° C. is satisfactory. However, the optimal temperature employed depends upon the particular first and second pyrolytic markers used.

When both markers are chromophoric markers, the process employed entails chemically treating the sample to release the first and second identifiers. The specific chemical treatment employed depends upon the particular first and second chromophoric markers used. For example, type group, the sample is treated with an appropriate acid (e.g., dichloroacetic acid) to remove the trityl or pixyl type group. The effluent of this acid treatment step is collected.

When the second marker is FMOC, the sample can be treated under basic conditions (e.g., with about 20% piperidine in DMF) to remove the FMOC group.

When the second marker is NPYS, the sample can be treated under neutral conditions (e.g., with a triphenyl phosphine reagent).

In both of the latter two examples, the effluent is also collected.

The first and second identifiers are then detected. The particular detection technique employed depends upon the type of first and second identifiers present.

When the identifiers are obtained by thermal decomposition, the identifiers can be detected by gas chromatography. Exemplary of the identifiers obtained by thermal decomposition include, but are not limited to, the following:

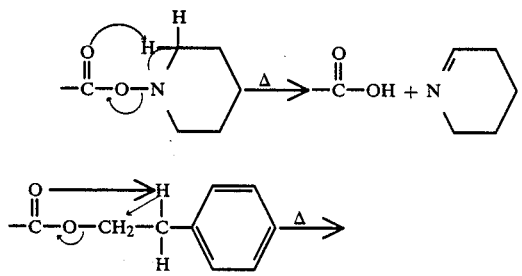

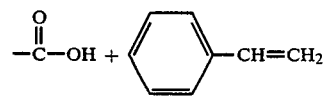

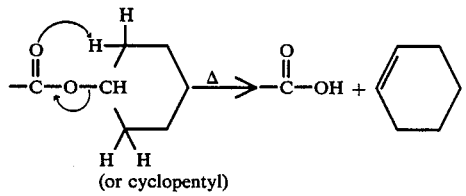

(or cyclopentyl)

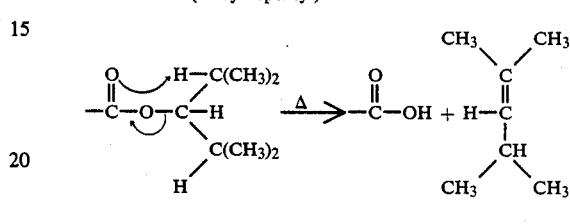

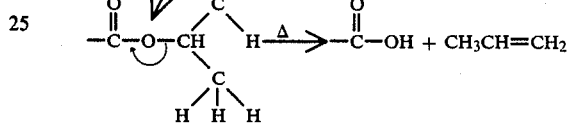

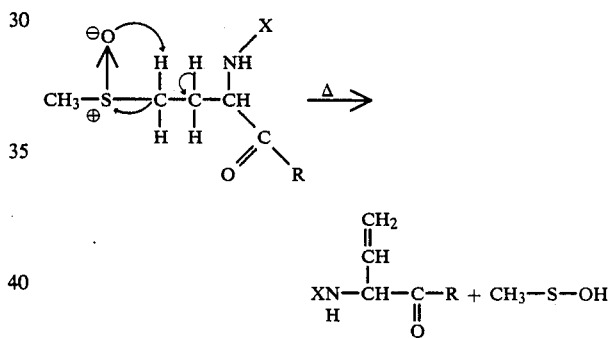

When the identifiers are chromophoric substances, the identifiers can be detected by determining the absorbance or transmittance or fluoresence of each collected effluent. (For example, FMOC can be detected at 310 nm and dimethoxytrityl can be detected at 490 nm). The effluents can be either checked separately or can first be mixed together before being evaluated. Because a combined effluent normalizes the results, it is preferred to first combine the effluents, if collected separately, prior to determining the absorbance or transmittance of the identifiers.

Once a determination of the relative amounts of first and second identifiers has been made, a comparison or ratio of these results indicates the completeness of the coupling reaction. The coupling of the initial amino acid can be assumed to be 100% complete and the ratio of second identifier to first identifier can be taken as the standard by which to determine whether the subsequent coupling steps are complete. If the ratio after coupling a subsequent amino acid is less than that of the initial ratio, then the subsequent coupling step is not complete. The subsequent coupling step can be repeated until the ratio obtained is the same as or as close to the initial ratio as desired.

After this comparison procedure, the composition of formula IV can be deprotected via conventional solid phase peptide systhesis procedures to yield a composition having the formula V

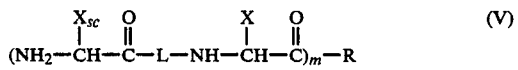 (V)

wherein $X_{sc}$, L, X, R, and m are as defined above.

To employ a method embodying features of the present invention to evaluate the completeness of the deprotection step, the second marker must be either the N-terminus blocking group of the initial amino acid or of a subsequent amino acid or a group which is also removed from the amino acid during the deprotection step.

When the second marker is the N-terminus protecting group, a direct determination is made of its presence or absence. In addition, when the second marker is the N-terminus protecting group, there is no need to further modify the amino acid prior to its coupling to the support matrix because the N-terminus protecting group is present on the amino acid during the coupling step. For these reasons, it is preferred that the second marker be the N-terminus protecting group.

After the deprotection step, a portion or sample of the support matrices is again taken. This sample can be processed in the same manner described with respect to the sample taken after the coupling step.

If the resulting ratio is zero, then the deprotection step is complete. However, if the resulting ratio is greater than zero, the deprotection step is incomplete. In this latter case, the deprotection step can be repeated until the ratio is zero or as close to zero as desired.

After this latter comparison procedure, subsequent N-terminus protected marked amino acids can be added following coupling/deprotection protocols employed in the solid phase synthesis of peptides. After each subsequent coupling and deprotection step, the above processing, detection, and comparison procedures can be employed to monitor the completion of each subsequent coupling and deprotection step.

During the course of the solid phase peptide synthesis, compositions having the formula VI

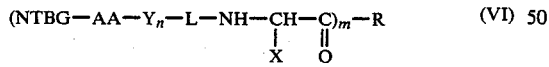 (VI)

are synthesized, wherein NTBG, L, X, R, and m are as defined above and AA is the terminal amino acid of the peptide, Y is an amino acid, and n is a positive integer. When n is greater than 1, each Y can be the same or a different amino acid. Exemplary compositions of formula VI having pyrolytic first and second markers attached thereto are as follows

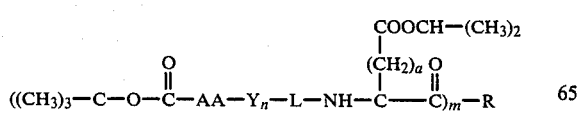

and

-continued

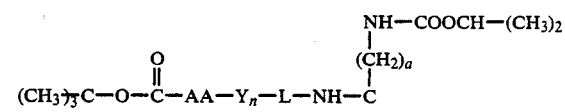

wherein AA, Y, L, R, m, and n are as defined above.

Deprotection of the composition of formula VI yields a composition having the formula VII

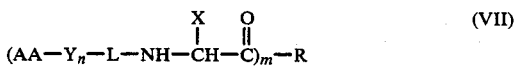 (VII)

wherein AA, Y, L, X, R, m, and n are as previously defined. Exemplary compositions of formula VII having pyrolytic markers attached thereto are as follows

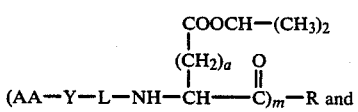 R and

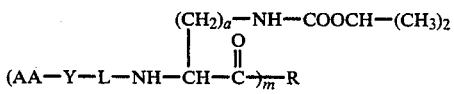

wherein AA, Y, L, R, m, and n are as defined above.

In another method embodying features of the present invention, the first marker is attached to a separate matrix which is used in association with a support matrix. More particularly, these marked, separate matrixes are present during the coupling and deprotection procedures employed in solid phase peptide synthesis. The samples taken after each coupling and deprotection step contain a mixture of the support matrix and the marked matrix. These samples are processed to release the first and second identifiers via the same techniques as set forth above. The detection and comparison steps in this method can be also the same as those employed above.

Exemplary marked matrixes which can be used in this latter described method include but are not limited to, those having the formula

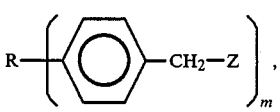,

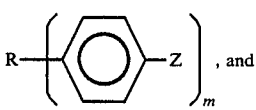, and

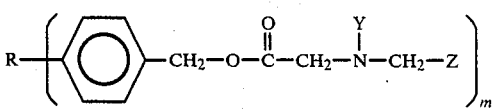

wherein R is a matrix; Z is a pyrolytic substituent; Y is selected from the group consisting of

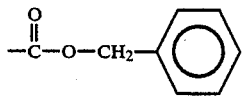

and acetyl; and m is at least 1.

Exemplary pyrolytic substituents include but are not limited to, those having the following formulas

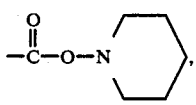

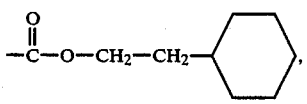

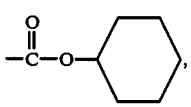

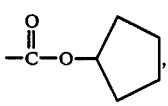

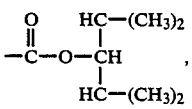

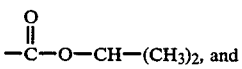

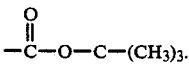

Marked matrixes having the formulas

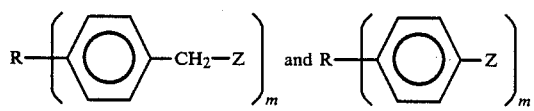

can be prepared by reacting a composition having the formulas

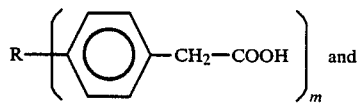

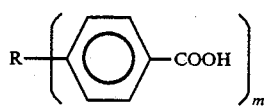

respectively, with an alcohol in the presence of DCC and DMAP. An emexplary alcohol is isopropanol.

EXAMPLES-INTRODUCTION

In the examples, melting points were taken on a Buchi melting point apparatus with a Cole-Parmer empeller and are uncorrected. Nuclear magnetic resonance (NMR) spectra were taken on a Varian EM360A brand spectrophotometer with tetramethylsilane as the internal standard. Pyrolysis of the resin peptide samples was carried out in a Chemical Data Systems Pyroprobe 150 brand thermal processing system. Gas chromatography (GC) of the pyrolyzed samples was carried out on a Beckman GC-45 brand flame ionization gas chromatograph fitted with a Supelco 2 m×⅛" Carbopack C (0.19 percent picric acid) brand column. Pyrograms were recorded and integrated on a Hewlett-Packard 3390A brand integrator. Peptide synthesis was performed on a Beckman Instrument model 990B peptide synthesizer. Amino acid analysis was performed on a Beckman Instrument model 121B amino acid analyzer. Hydrogenations were carried out on a Parr low-pressure shaker type reaction apparatus. Analytical thin layer chromatography (TLC) was performed with E. Merck pre-coated F-254 brand silica gel 60 (0.25 mm×5 cm×20 cm) (TLC) plates and was visualized under ultra violet (UV) light at 25 nm. Boc-amino acids unless otherwise specified were purchased from the Protein Research Foundation (Japan). Benzhydrylamine resin (BHA resin) hydrochloride (0.69 meg/gm) was obtained from Beckman Instruments. All solvents and bulk chemicals were reagent grade and were not further purified except for dimethylaminopyridine (DMAP), which was purchased from Aldrich and was recrystallized from ethyl acetate (EtOAc) prior to use.

EXAMPLE 1

Preparation of BOC-(Beta-isopropyl) Aspartic Acid-alpha-benzyl ester (II)

BOC-aspartic acid-alpha-benzyl ester (100 g, 0.31 mol) was dissolved in 120 ml of methylene chloride ($CH_2Cl_2$) and to this solution was added a solution of 57.8 g (0.28 mol) of dicyclohexylcarbodiimide (DCC) in 280 ml of $CH_2Cl_2$ over a period of 10 min followed by the addition of 34.2 g (0.28 mol) of DMAP in 50 ml of $CH_2Cl_2$. Then to the stirred reaction mixture 19.0 g (0.31 mol) of isopropyl alcohol (IPA) were added, the stirring taking place for 48 hours.

The reaction mixture was filtered to remove precipitated dicyclohexylurea (DCU), and the resulting cake was washed with $CH_2Cl_2$. The combined filtrates were evaporated to a residual oil. The residue was dissolved in 400 ml of diethyl ether ($Et_2O$) and the solution washed in a separatory funnel with the following sequence of washes at 100 ml per wash: 2 times with aqueous 10% sodium carbonate ($Na_2CO_3$); 2 times with $H_2O$; 2 times with aqueous 0.5M hydrochloric Acid (HCl); 3 times with $H_2O$; and 2 times with saturated aqueous sodium chloride (NaCl). The organic layer was dried over anhydrous magnesium sulfate ($MgSO_4$). The drying agent was removed by filtration and the filtrate evaporated. The weight of the resulting product was 79 g which represents a 70% yield. TLC (95/5/3; ($CH_2Cl_2$/MeOH/HOAc) gave a major spot at $R_f$ 0.85. NMR deuterochloroform ($CDCl_3$): gamma 7.34 (s, 5) 5.52 (m, 1), 5.16 (s, 2), 5.05 (m, 1), 4.8 (m, 1), 2.88 (m, 2), 1.4 (s, 9), 1.15 (d, 6).

EXAMPLE 2

Preparation of BOC-(Beta-isopropyl)-aspartic acid (III)

II (79 g, 0.22 mol) was dissolved in 260 ml of methanol ($CH_3OH$) and the solution was placed in a Parr reactor vessel. The vessel was flushed with nitrogen while adding 29.75 g of 10% palladium catalyst (Pd-C) premoistened with HOAc). The vessel was placed in the Parr instrument and flushed with nitrogen (3 times at 15 psi) and with hydrogen (3 times at 60 psi) and agitated with hydrogen at 60 psi for 24 hours. The vessel was flushed with nitrogen and the reaction mixture filtered through Celite brand cellulose filtration aid. The filtrate was evaporated and the residue dissolved in 200 ml of ethyl acetate (EtOAc). This solution was extracted with two 200 ml portions of aqueous 10% $Na_2CO_3$. The aqueous layers were combined and acidified with aqueous 1M HCl to pH 2. The solution was then extracted with three 300 ml portions of (EtOAc). The combined organic layers were washed with 100 ml of $H_2O$, and dried over anhydrous $MgSO_4$. The drying agent was removed by filtration and the filtrate was evaporated. The residue was dissolved in $Et_2O$ and hexane was slowly added to the solution until it became turbid. The product precipitated upon standing (16 hours). Filtration yielded a white solid. TLC ($CH_2Cl_2$/MeOH/HOAc; 95/5/3) showed a single spot with $R_f 0.05$. NMR ($CCDl_3$): gamma 2.9 (m, 3), 1.49 (s, 9), 1.25 (d, 6). Elemental analysis: Actually Found (Theoretically present): C, 52.40 (52.36); H, 7.87 (7.63); N, 5.06 (5.09).

EXAMPLE 3

Preparation of BOC-(Beta-isopropyl) aspartyl-benzhydrylamine (BHA resin (IV)

BHA resin hydrochloride (26.93 g, 18.58 mmol) was placed in the reaction vessel of a Beckman 990B brand peptide synthesizer and subjected to the following standard protocol to obtain IV.

It was stirred two times for five minutes each with 250 ml of $CH_2Cl_2$, two times for five minutes each with 10 percent triethylamine (TEA) in $CH_2Cl_2$, and four times for two minutes each with 250 ml of $CH_2Cl_2$. III (7.7 g, 27.9 mmol) in 200 ml of $CH_2Cl_2$ was mixed with the resin and then hydroxybenztriazole (HOBT) (2.5 g, 18.6 mmol) was added. DCC (27.9 mmol) was added as a 0.5 molar solution in $CH_2Cl_2$ The mixture was stirred for six hours. The reaction mixture was filtered and the coupling reaction was repeated for 12 hours using the same amount of reagents. The filtered resin was then stirred two times, two minutes each, with 250 ml of 33% EtOH in $CH_2Cl_2$, two times, for two minutes each, with 250 ml N-methylpyrrolidone (NMP), three times, for two minutes each, with 250 ml of $CH_2Cl_2$ and finally two times for two minutes each, with 250 ml EtOH. The Kaiser ninhydrin test was negative. The resin was dried in a vacuum over pentoxide $P_2O_5$, wt. 31.08 g. GC pyrolysis data (area percent) isobutene 67.97; propene 32.03.

EXAMPLE 4

Preparation of-Alpha-BOC-valyl-4-(oxymethyl) Phenylacetic Acid (VII)

VII was prepared by a procedure previously described by Tam et al., *Synthesis*, 12: 955-957 (1979). A white solid was obtained, melting point (m.p.) 75°-78° C. (literature 74°-78° C.) The NMR spectrum ($CDCl_3$): gamma 7.3 (s, 4), 5.1 (s, 2), 4.2 (m, 1), 3.6 (s, 2), 2.05 (m, 1), 1.4 (s, 9), 0.9 (d, 6).

EXAMPLE 5

Preparation of N-[BOC-valyl-4-(oxymethyl)phenylacetyl]-(beta isopropyl)aspartyl (N-BOC-val-PAMPRO) BHA Resin (VI)

IV (3.0 g, 1.2 mmol) was placed in the automated synthesizer and the BOC group removed according to the following protocol.

The resin (filtering after each treatment) was stirred for three minutes with 60 ml of a 50% trifluoroacetic acid (TFA) $CH_2CL_2$ solution. The 50% TFA/$CH_2Cl_2$ treatment was repeated for 30 minutes. The resin was then stirred four times with 60 ml of $CH_2Cl_2$ for two minutes each wash, neutralized by stirring two times, 10 minutes each time, with 60 ml of a 10% TEA solution in $CH_2Cl_2$, and stirred five times, for two minutes each, with 60 ml of $CH_2Cl_2$.

The deprotected resin (V) obtained by the above procedure was mixed with a solution of VII (1.1 g, 3.0 mmol) in 50 ml of $CH_2Cl_2$ and 3.0 mmol of DCC (6 ml of a 0.5M solution in $CH_2Cl_2$) and the reaction mixture was stirred for six hours. After filtering the reaction mixture the coupling reaction was repeated for 12 hours using the same proportion of reactants. After filtration the resin was washed two times with 60 ml of 33% ethanol (EtOH) in $CH_2Cl_2$, two times with 60 ml of NMP, four times with 60 ml of $CH_2Cl_2$, and two times with 60 ml of EtOH. The resin was dried in a vacuum over $P_2O_5$. The Kaiser ninhydrin test was negative. GC pyrolysis data (area percent): isobutene 58.41; propene 41.59. These results are set forth in Table II.

EXAMPLE 6

Preparation of N-[BOC-Leu-Ala-Gly-Val-4-(oxymethyl)- phenylacetyl]-(Beta-isopropyl)aspartyl Compound VI (2.0 g, 0.6 mmol) was deprotected with 50% TFA in $CH_2Cl_2$, neutralized with 10% TEA in $CH_2Cl_2$ as described in the deprotection of IV. The deprotected resin was reacted with BOC-glycine according to the following protocol.

A solution of BOC-glycine (0.32 g, 1.8 mmol) in 15 ml of $CH_2Cl_2$ was stirred for two minutes with the resin in an automated peptide synthesizer. To this mixture were added 3.6 ml of a 0.5M solution of DCC in $CH_2Cl_2$ (1.8 mmol of DCC). The reaction mixture was stirred for six hours and the reaction vessel drained. The resin was subjected to the following treatment: Stir two times, for two minutes each, with 20 ml of a 33% solution of EtOH in $Ch_2Cl_2$, stir 2 times, for two minutes each, with 20 ml of NMP, and stir 4 times, for two minutes each, with 20 ml of $CH_2Cl_2$. The Kaiser test was negative. The resin was deprotected according to the procedure set forth in Example 5. BOC-alanine and BOC-leucine were added following the deprotection/coupling/deprotection/coupling protocols described in this example. Following each deprotection and coupling reaction, 50 to 100 mg of resin peptide were removed and examined by the Kaiser ninhydrin test, by amino acid analysis (AAA), and by a pyrolytic method embodying features of the present invention. These results are set forth in Tables I and II.

EXAMPLE 7

Application of Method to a Resin Peptide Synthesis

Monitoring of each reaction step by a method embodying features of the present invention was carried out in the following manner. An aliquot (about 50 mg) of each washed and drained resin peptide produced in Examples 5 and 6 was withdrawn with a 2 mm bore flexible capillary tube, placed in a 10 ml test tube and evaporated under vacuum for 5 minutes. Several milligrams of dry resin peptide beads were withdrawn with a 1.5 mm×90 mm closed end glass capillary tube, the beads centered at about 0.5-1.0 cm from the closed end of the tube, the capillary cleanly broken at 1-2 cm from the closed end, then placed within a spiral platinum wire coil at the end of a Chemical Data Systems Pyroprobe 150 brand thermal processing system. The sample was first pyrolyzed at 100° C. for 40 seconds (two 20 second pulses) to vaporize trapped methylene chloride. Next, the sample was pyrolyzed for 80 seconds by heating the wire cell with four 20 second pulses of electrical current at a high end temperature setting of 500° C. The resultant gases were injected directly from the heating chamber onto a 2 m×⅛" carbopack (0.19 percent picric acid) GC column. The column temperature was set at 70±5° C. and the nitrogen carrier gas flow rate set at 40±3 ml/min. Chromatograms (pyrograms) were recorded and peak areas directly integrated on a Hewlett-Packard 3390A brand integrator. As a second monitoring method the Kaiser ninhydrin test was performed at each stage of the synthesis. In addition, amino acid

TABLE I

| Amino Acid Analysis Data of BOC—Leu—Ala—Gly—Val—PASPRO—BHA Resin | | |
|---|---|---|
| Amino Acid | Molar Ratio | Theory |
| Leu | 1.04 | 1 |
| Ala | 1.01 | 1 |
| Gly | 1.03 | 1 |
| Val | 1.00 | 1 |

Hydrolysis with propionic acid: 6N HCl (1:1) for 4 hours.

TABLE II

| Pyrolysis Results of BOC—Leu—Ala—Gly—Val—PAMPRO—BHA Resin | | | | | | |
|---|---|---|---|---|---|---|
| | | | | Percent Completion | | |
| Peptide Resin | Isobut. (area) X | Propene (Area) Y | Ratio X/Y | Coupling Reaction | Deprotection Reaction | Kaiser Test (Color) |
| BocVal | 58.41 | 41.59 | 1.4 | 100.0 | | Yellow (−) |
| H—Val | 00.00 | 100.00 | 0 | | 100.00 | Purple (+) |
| BocGly—Val | 57.95 | 42.05 | 1.38 | 98.51 | | Yellow (−) |
| H—GlyVal | 00.00 | 100.00 | 0 | | 100.00 | Purple (+) |
| BocAla—GlyVal | 57.31 | 42.69 | 1.34 | 97.1 | | Yellow (−) |
| H—AlaGly—Val | 00.00 | 100.00 | 0 | | 100.00 | Purple (+) |
| BocLeu—AlaGlyVal | 57.11 | 42.89 | 1.33 | 99.25 | | Yellow (−) |

Although the present invention has been described in considerable detail with reference to certain versions thereof, other versions are possible. For example, first markers can be attached to both the support matrix and to a separate matrix that is used in association with the support matrix. In addition, the method of the present invention can also be used as a qualitative monitoring tool. Therefore, the spirit and scope of the appended claims should not be limited to the description of the preferred versions contained herein.

What is claimed is:

1. A composition of matter having the formula:

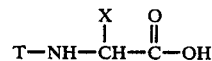

wherein:

T is H or a blocking group; and

X is selected from the group consisting of —(CH$_2$)$_a$—NH—Z and —(CH$_2$)$_a$—Z, wherein a is O or a positive integer and Z is selected from the group consisting of:

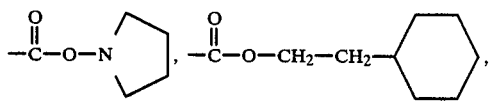

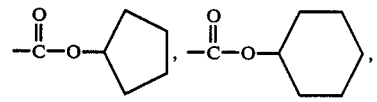

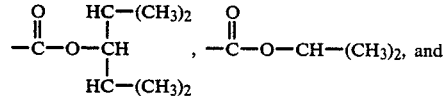

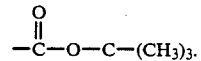

2. The composition of claim 1 wherein the blocking group is selected from the group consisting of t-butyloxycarbonyl, 2-(4-biphenylyl)-2-propyloxy carbonyl, alpha-2,4,5-tetramethylbenzyloxy carbonyl, 2-phenyl-2-propyloxycarbonyl, and 2-(3,5-dimethoxyphenyl)-2-propyloxycarbonyl.

3. The composition of claim 1 having the formula:

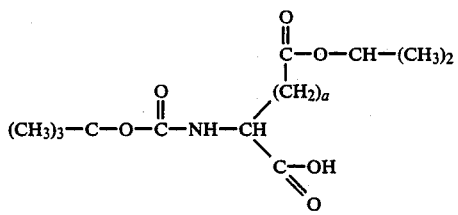

4. A composition of matter having the formula:

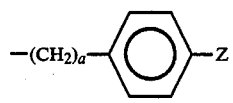

wherein:

T is H or a blocking group;
X is selected from the group consisting of:

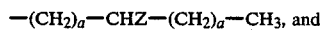

—(CH$_2$)$_a$—Z,

—(CH$_2$)$_a$—CHZ—(CH$_2$)$_a$—CH$_3$, and

—(CH$_2$)$_a$—Z a is 0 or a positive integer; and
Z is selected from the group consisting of:
- —O—trityl,
- —S—trityl,
- —O—pixyl,
- —S—pixyl, and homologs and analogs thereof.

5. The composition of claim 4 wherein the blocking group is selected from the group consisting of fluorenyl methyloxy carbonyl and 3-nitro-2-pyridine sulfenyl groups.

6. A composition of matter having the formula

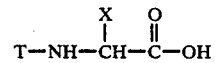

wherein:

T is H or a blocking group;
X is selected from the group consisting of —(CH$_2$)$_a$—NH—Z and —(CH$_2$)$_a$—Z, wherein a is 0 or a positive integer and Z is $$-\overset{\overset{O}{\|}}{C}-O-CH_2-(CH_3)_2.$$

7. The composition of claim 6 wherein T is 2-(4-biphenylyl)-2-propyloxy carbonyl.

8. A composition of matter having the formula

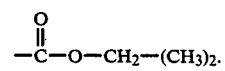

wherein:

T is H or a blocking group;
X is selected from the group consisting of —(CH$_2$)$_a$—NH—Z and —(CH$_2$)$_a$—Z, wherein a is 0 or a positive integer and Z is $$-\overset{\overset{O}{\|}}{C}-O-C-(CH_3)_3.$$

9. The composition of claim 8 wherein T is 2-(3,5-dimethoxyphenyl)-2-propyloxycarbonyl.

10. A composition of matter having the formula

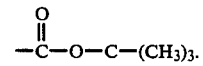

wherein:

T is H or a blocking group;
X is —(CH$_2$)$_a$—Z;
a is 0 or a positive integer; and
Z is selected from the group consisting of —O—trityl and homologues and analogues thereof.

11. The composition of claim 10 wherein the blocking group is selected from the group consisting of fluorenyl methoxy carbonyl and 3-nitro-2-pyridine sulfenyl groups.

* * * * *